(12) United States Patent
Richie, Jr.

(10) Patent No.: US 8,683,717 B2
(45) Date of Patent: Apr. 1, 2014

(54) SUPPORT FOR INCLUSION IN ARTICLE OF FOOTWEAR AND METHOD FOR RAISING THE ARCH OF A PERSON'S FOOT

(76) Inventor: Douglas H. Richie, Jr., Long Beach, CA (US)

( * ) Notice: Subject to any disclaimer, the term of this patent is extended or adjusted under 35 U.S.C. 154(b) by 542 days.

(21) Appl. No.: 12/958,005

(22) Filed: Dec. 1, 2010

(65) Prior Publication Data

US 2011/0126427 A1   Jun. 2, 2011

Related U.S. Application Data

(60) Provisional application No. 61/265,471, filed on Dec. 1, 2009.

(51) Int. Cl.
*A43B 7/22* (2006.01)
*A61F 5/14* (2006.01)
*A43B 7/14* (2006.01)
*A43B 13/38* (2006.01)

(52) U.S. Cl.
USPC .......... 36/91; 36/43; 36/145; 36/172; 36/174; 36/176; 36/180

(58) Field of Classification Search
USPC ............... 36/43, 44, 145, 172, 174, 176, 166, 36/178, 180
See application file for complete search history.

(56) References Cited

U.S. PATENT DOCUMENTS

| | | | | |
|---|---|---|---|---|
| 1,187,578 A | * | 6/1916 | Watrous | 36/176 |
| 1,958,097 A | * | 5/1934 | Shaw | 36/144 |
| 2,116,579 A | * | 5/1938 | Leydecker | 36/178 |
| 2,190,568 A | * | 2/1940 | Lattemann | 36/145 |
| 2,193,704 A | * | 3/1940 | Vaughn | 36/145 |
| 2,252,936 A | * | 8/1941 | Leydecker | 12/142 N |
| 4,333,472 A | * | 6/1982 | Tager | 36/140 |
| 4,642,911 A | * | 2/1987 | Talarico, II | 36/30 R |
| 4,682,425 A | * | 7/1987 | Simmons | 36/44 |
| 4,685,227 A | * | 8/1987 | Simmons | 36/127 |
| 5,129,395 A | * | 7/1992 | Hoffmann | 36/145 |
| 5,345,701 A | * | 9/1994 | Smith | 36/144 |
| 6,874,258 B2 | * | 4/2005 | Clough et al. | 36/144 |
| 7,069,665 B1 | * | 7/2006 | Adriano | 33/515 |
| 7,299,568 B2 | * | 11/2007 | Tager | 36/140 |
| 7,441,349 B2 | * | 10/2008 | Seydel et al. | 36/114 |
| 2002/0005000 A1 | * | 1/2002 | Choi | 36/144 |

OTHER PUBLICATIONS

C.B. Blackwood, et al., "The Midtarsal Joint Locking Mechanism," Foot & Ankle International 2005, 26:1074-1080.

(Continued)

*Primary Examiner* — Khoa Huynh
*Assistant Examiner* — Katharine Gracz
(74) *Attorney, Agent, or Firm* — Caesar, Rivise, Bernstein, Cohen & Pokotilow, Ltd.

(57) ABSTRACT

A support arranged for disposition within a shoe, boot or sandal, to raise the arch of the foot by everting the forefoot and inverting the rearfoot, thereby locking the midtarsal joint. The support basically comprises a base portion and a wedge portion. The base portion has an upper surface on which the wedge portion is disposed. The wedge portion includes a medial side edge and a lateral side edge and extends from the base of all five metatarsals of the person's foot to the heads of all five metatarsals. The wedge portion tapers in thickness from at least the midline of the wedge portion to the medial side edge. The wedge portion includes an anterior portion that is tapered to the sulcus section of the wearer's foot.

14 Claims, 1 Drawing Sheet

(56) References Cited

OTHER PUBLICATIONS

H. Elftman, "The Transverse Tarsal Joint and Its Control," Clin. Othop 1960, 6: 41-45.

G.F. Kogler, et al., "The Influence of Medial and Lateral Placement of Orthotic Wedges on Loading of the Plantar Aponeurosis," Journal of Bone and Joint Surgery 1999, 81A: 1403-1413.

S.K. Sarrafian, "Functional Characteristics of the Foot and Plantar Aponeurosis under Tibiotalar Loading," Foot Ankle 1987, 8: 4-9.

* cited by examiner

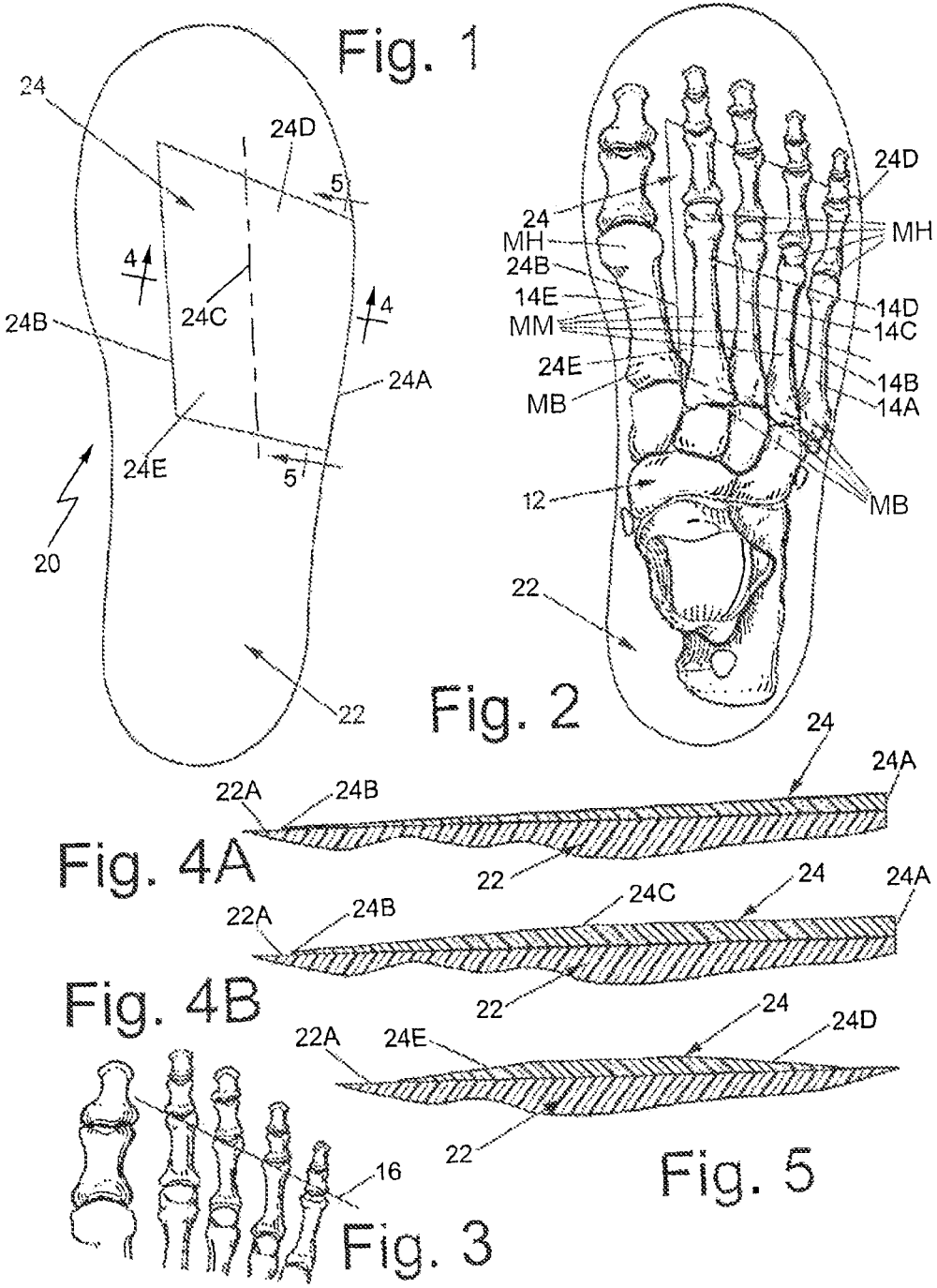

SUPPORT FOR INCLUSION IN ARTICLE OF FOOTWEAR AND METHOD FOR RAISING THE ARCH OF A PERSON'S FOOT

CROSS-REFERENCE TO RELATED APPLICATIONS

This application claims priority from Provisional Application Ser. No. 61/265,471, filed on Dec. 1, 2009, entitled Support for Inclusion in Article of Footwear and Method for Raising the Arch of a Person's Foot, which application is assigned to the same assignee as this application and whose disclosure is incorporated by reference herein.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISK

Not Applicable

FIELD OF THE INVENTION

This invention relates generally to devices for use in footwear and more particularly to a support arranged for disposition within an article of footwear, e.g., a shoe, boot or sandal, to effect the raising of the arch of a person's foot.

BACKGROUND OF THE INVENTION

As is known to those skilled in the art an orthotic is an apparatus used to support, align, prevent, or correct deformities or to improve the function of movable parts of the body. A foot orthotic can take the form of a simple metatarsal pad, a heel pad or an arch support. Arch supports are worn for comfort and for medical purposes. Arch failure or "weak arches" are known to cause a myriad of foot pathologies including bunions, hammertoes, tendon strain and ligament strain. Thus, arch supports are commonly prescribed by health professionals to treat many forms of foot pain or foot deformity.

Traditional arch supports achieve their clinical benefit by providing mechanical support to a limited area of the foot, namely the bones which comprise the medial longitudinal arch. This support is provided by a foot bed which has a raised contour which is generally shaped to conform to an "average" shape of the arch of the human foot. However, there is no universal shape of the arch of the foot of humans. The length, width and height of the arch of the human foot vary widely among all human beings.

Custom foot orthotic devices are manufactured with a goal to mold the device to the specific shape of the foot of the user. While the comfort of such a molded device is superior to a non-custom orthotic, the medical benefits of a custom foot orthotic have not been clearly demonstrated in numerous studies published in the medical literature. In fact, accurate molding of the arch of an orthotic to the foot of the user has not been shown to significantly improve alignment or prevent foot pathology. Custom orthotic devices may have benefit for reasons other than simple arch support. True functional foot orthotics correct deformities which cause the foot to compensate by rolling inward at the ankle joint (pronation) or outward (supination). Also, molding of a custom orthotic to the heel of the user, utilizing a deep heel cup is thought to improve alignment and function of the foot.

While enhancing stability of the arch of the foot is a common goal in the use of foot orthotic devices, achieving that goal is more difficult than one would expect. In this regard, the human foot has a narrow range of tolerance of pressure applied by a support to the tissues under the bone structures of the medial arch. Therefore, clinicians have looked to other methods of "indirectly" raising the arch of the foot with orthotic devices. One well accepted method is an impression casting technique where the clinician will purposefully "lock" the position of the midtarsal joint of the foot. The midtarsal joint is the primary movement interface of the bones of the arch of the foot. This joint can be aligned in more stable manner, simply by positioning certain bone segments of the foot. This is known as the "locking mechanism" of the midtarsal joint.

The locking mechanism of the midtarsal joint was originally described by H. Elftman in his article entitled "The Transverse Tarsal Joint and Its Control", appearing in Clin. Othop 1960, 16:41-45 and that has been validated and embraced by foot health professionals for the past 60 years. It has also recently been validated by C. B. Blackwood, T. J. Yuen, B. J. Sangeorzan and W. R. Ledoux in their article entitled "The Midtarsal Joint Locking Mechanism" appearing in Foot Ankle Int. 2005, 26: 1074-1080.

As is known the locking mechanism of the midtarsal joint is accomplished by two simple movements of the bone segments which lie on either side of the midtarsal joint: (1) the rearfoot or calcaneus (heel bone) is inverted (twisted towards the midline of the body), and (2) the forefoot (metatarsals) is everted (twisted away from the midline of the body. Therefore, to "lock" the midtarsal joint of the left foot: the forefoot is twisted in a clockwise direction, while the rearfoot is twisted in a counter clockwise direction. In practice, to "lock" the midtarsal joint of the right foot, the right forefoot is twisted in a counter clockwise direction while the right rearfoot is twisted in a clockwise direction. The locking of the midtarsal joint of the left foot is accomplished by twisting the left forefoot in the clockwise direction while the left rearfoot is twisted in the counter clockwise direction. This twisting movement of two segments of the human foot has long been recognized as a motion and ultimate position of the foot which has improved stability and function. A locked and stable midtarsal joint is thought to provide more leverage for propulsion during gait.

It is also known that a locked and stable midtarsal joint will raise the arch of the foot while an unlocked midtarsal joint will lower the arch of the foot. Therefore, an indirect way to raise the arch of the foot, without actually pushing against the arch of the foot would be a mechanism which "locks" the midtarsal joint.

The locking mechanism and effects of stability on the arch of the foot was described in a different way by a noted anatomist and orthopedist, S. K. Sarrafian M.D. in his article entitled "Functional Characteristics of the Foot and Plantar Aponeurosis under Tibiotalar Loading", appearing in Foot Ankle 8: 4-17, 1987. In that article Dr. Sarrafian observed that the human foot was constructed like a "twisted plate" whereby the bones of the rearfoot (i.e., talus and calcaneus) were oriented in a vertical alignment, while the bones of the forefoot were oriented in a horizontal alignment. Dr. Sarrafian also noted that when the twisted plate arrangement of the bones of the foot was further twisted, i.e., the forefoot was twisted in an everted direction while the rearfoot was twisted in an inverted direction the height of the arch of the foot was raised while the length of the arch was shortened.

Compared to primates, the human foot has bones in this twisted plate alignment which allows the formation of the medial and lateral arches, and allows the mechanical stability of the human foot which is not found in any other animal population.

Whether the bones of the human foot are moved in a way to lock the midtarsal joint, or to "twist the plate" the force or movement applied against the forefoot and rearfoot are the same: the forefoot is twisted in an everted direction, while the rearfoot is twisted in an inverted direction. The end result is a more stable foot structure which has less of a load on the passive soft tissues which normally support the arch.

While knowledge of the osseous locking mechanism of the human foot and the "twisted plate" phenomenon of the raising of the height of the arch has been known and published for at least 20 years, there has been no technology developed which would position the foot according to these principles. Specifically, there has been no foot orthotic device designed to twist the bone structure of the human foot in such a way to indirectly raise the height of the medial longitudinal arch and lock the midtarsal joint for stability.

In an article by Kogler G F, Veer F B, Solomonidis S E, Paul J P entitled: "The influence of medial and lateral placement of orthotic wedges on loading of the plantar aponeurosis", Journal of Bone and Joint Surgery 81-A: 1403, 1999, a forefoot lateral wedge was used in a study to measure strain in the plantar aponeurosis, which is a primary ligament which supports the arch. The wedge was described as being commonly used clinically and had an angle of 6 degrees and a thickness of 5, 6 or 7 mm. The wedge was placed starting at mid-shaft of the metatarsals and extended all the way to the end of the toes. The authors reference a locking effect of the wedge solely to the calcaeal-cuboid joint (which is one of two joints in the midtarsal joint) and do not reference a change of arch height. Their primary conclusion is about relieving strain in the plantar aponeurosis.

Thus, a need exists for a device which can be incorporated into an article of footwear for indirectly raising the arch of the wearer's foot by locking the midtarsal joint. The subject invention addresses that need and is arranged to be incorporated in any type of footwear, e.g., shoe, sandal, etc.

All references cited herein are incorporated herein by reference in their entireties.

SUMMARY OF THE INVENTION

In accordance with one aspect of this invention there is provided a support arranged for disposition within an article of footwear, e.g., a shoe, boot or sandal, to effect the raising of the arch of a person's foot by everting the forefoot of the person and inverting the rearfoot of the person, thereby locking the person's midtarsal joint. The support basically comprises a base portion and a wedge portion.

The base portion extends for substantially the length and width of the person's foot and having an upper surface and a lower surface. The wedge portion is disposed on or forms a portion of the upper surface of the base portion and has a lateral side edge and a medial side edge. The wedge portion extends from the base of all five metatarsals of the person's foot to the heads of all five metatarsals, whereupon the wedge portion is thickest at the midshaft of the fifth metatarsal at the lateral side edge and thinnest at the base of all the metatarsals and the lateral aspect of the first metatarsal. The wedge portion includes an anterior portion and a posterior portion. The anterior portion tapers in thickness to the sulcus section of the person's foot.

In accordance with yet another preferred aspect of this invention the base portion comprises either an in-shoe/in-boot/in-sandal foot bed, an insole for a shoe, boot or sandal, or the lining of a shoe, boot or sandal.

In accordance with still another preferred aspect of this invention the wedge portion comprises EVA foam.

In accordance with another aspect of this invention a method of raising the arch of a person's foot by everting the forefoot of the person and inverting the rearfoot of the person, thereby locking the person's midtarsal joint is provided using a support having a wedge portion constructed as discussed above.

DESCRIPTION OF THE DRAWING

FIG. 1 is a top plan view of one exemplary embodiment of an insole incorporating a wedge constructed in accordance with this invention;

FIG. 2 is a view similar to FIG. 1, but showing the foot of a person when disposed on the insole when in use;

FIG. 3 is a reduced plan view of a portion of the foot of a person showing the angle of the sulcus region (which corresponds to the proximal interphalangeal joints of the toes or the head of the proximal phalanges);

FIG. 4A is an enlarged sectional view taken along line 4-4 of FIG. 2 to show one exemplary embodiment of the wedge portion of this invention;

FIG. 4B is an enlarged sectional view also taken along line 4-4 of FIG. 2 to show another exemplary embodiment of the wedge portion of this invention; and FIG. 5 is an enlarged sectional view taken along line 5-5 of FIG. 2.

DETAILED DESCRIPTION OF THE PREFERRED EMBODIMENT

Referring now to the various figures of the drawing wherein like reference characters refer to like parts, there is shown at 20 in FIG. 1 one exemplary embodiment of a support, arranged for disposition within an article of footwear, e.g., shoe, boot, sandal, etc. (not shown), to effect raising of the arch of a person's foot 12 (FIG. 2). The support of the subject invention is designed to be incorporated into a foot orthotic (in-shoe foot bed) or can be affixed to an already manufactured shoe insole, orthotic foot bed or into the lining of a shoe, boot or sandal. Moreover, it is specifically configured to provide a specific support or lifting effect to certain key areas of the human foot which will result in an elevation of medial arch and a reduced strain on the supportive tissues of the arch. Thus, the support of the subject invention is intended to provide comfort to the human foot as well as relief of certain medical conditions, as will be described later.

As best seen in FIGS. 1, 2, and 4A, 4B and 5, the exemplary support 20 is in the form of an in-shoe foot bed or insole that is arranged to be inserted into the shoe, boot or sandal, or placed on the top surface of the footwear's foot bed or incorporated into a foot orthotic device. The support 20 basically comprises a base portion 22 and a wedge portion 24, each of which will be described in detail later. Suffice for now to state that the base portion 22 includes a bottom surface (not shown) and a top surface 22A. The bottom surface is arranged to be disposed on the inner surface of the shoe or other footwear (not shown) in which the support 20 to be used. The wedge portion 24 makes up, e.g., is disposed on, the top surface 22A of the base portion 22 and is intended to elevate the lateral aspect of the wearer's foot 12 from the weight bearing surface.

As best seen in FIG. 1, the wedge portion 24 includes a lateral side edge 24A and a medial side edge 24B and is located on the forefoot region of the base portion 22 so that it extends laterally-to-medially from approximately the second metatarsal 14D to the fifth metatarsal 14A (see FIG. 2). The thickness of the wedge tapers downward at a constant angle from its maximum height at its lateral side edge 24B to virtually no thickness at its medial side edge 24A, where it meets the base portion 22. Thus, in the exemplary embodiment, shown in FIG. 4A, the top surface of the wedge portion is in the form a gradual downward slope from the $5^{th}$ metatarsal 14A, whereby the $5^{th}$ metatarsal is higher off the ground than the $4^{th}$ metatarsal 14B, which is higher off the ground than the $3^{rd}$ metatarsal 14C, which is higher off the ground than the $2^{nd}$ metatarsal 14D. Since the wedge is not located under the first metatarsal 14E, the height of the first metatarsal off the ground is just slightly less than the 2nd metatarsal 14D (the $2^{nd}$ metatarsal is located a slight distance laterally of the lateral edge of the wedge it is thus slightly elevated above that edge).

One exemplary embodiment of the wedge portion shown in FIG. 4A has a width (lateral-to-medial distance) of approximately 3 inches (7.6 cm), a length of approximately 5 inches (12.7 cm), and a maximum thickness at the medial edge of 0.25 inch (6.4 mm). With such an embodiment the angle of the wedge from the lateral side to the medial side is approximately 4.76 degrees. As should be appreciated by those skilled in the art, the dimensions of the wedge portion are dependent upon the size of the wearer's foot. Thus, other sizes of wedge portions are contemplated within the context of this invention. For example, the length of the wedge portion may be in the range of approximately 4 inches to approximately 5 inches (10.2 to 12.7 cm). The width of the wedge portion may be in the range of approximately 2 inches to approximately 3 inches (5.1 to 7.6 cm). The height of the wedge portion may be in the range of approximately 1/8 inch to approximately 1/4 inch (3.2 to 6.4 mm).

In FIG. 4B there is shown an alternative exemplary embodiment of a wedge portion 24 constructed in accordance with this invention. In that embodiment approximately one half of the width of the wedge portion 24 from its medial side edge 24A inward to approximately the midline 24C (FIG. 1) of the wedge portion 24 is of a constant thickness, and then tapers downward to the medial side. Thus, in this embodiment the $5^{th}$ metatarsal 14A and the $4^{th}$ metatarsal 14B are both at the same height higher off the ground than the $3^{rd}$ metatarsal 14C, which is higher off the ground than the $2^{nd}$ metatarsal 14D, which is higher off the ground than the $1^{st}$ metatarsal 14E.

An exemplary embodiment of the alternative wedge portion shown in FIG. 4B also has a width (lateral-to-medial distance) of approximately 3 inches (7.6 cm), a length of approximately 5 inches (12.7 cm), and a maximum thickness at the medial edge of 0.25 inch (6.4 mm). With such an embodiment the angle of the wedge from the lateral side to the medial side is approximately 9.46 degrees. As discussed above other sizes of wedge portions for this embodiment are also contemplated within the context of this invention. For example, the length of the wedge portion may be in the range of approximately 4 inches to approximately 5 inches (10.2 to 12.7 cm). The width of the wedge portion may be in the range of approximately 2 inches to approximately 3 inches (5.1 to 7.6 cm). The height of the wedge portion may be in the range of approximately 1/8 inch to approximately 1/4 inch (3.2 to 6.4 mm).

As best seen in FIG. 2 the wedge portion 24 extends from the base MB of all five metatarsals 14A-14E to the heads MH of all five metatarsals. Moreover, the wedge portion 24 is tapered from its highest point at midshaft MM of the $5^{th}$ metatarsal 14E to its thinnest section at the base of all metatarsals, and the lateral aspect of the 1st metatarsal 14A. Further still as best seen in FIG. 5 the forward, or anterior part 24D of the forefoot section of the wedge portion 24 is also tapered to the sulcus section 16 (FIG. 3) of the foot where the phalanges of the toes meet the metatarsals. The rear or posterior portion 24E of the wedge portion 24 is also tapered at a similar angle to the anterior portion. In the exemplary embodiment shown the taper at the anterior (sulcus) 24D region of the wedge portion extends for approximately 1/3 of the length of the wedge portion, while the taper at the posterior region 24E of the wedge portion also extends for approximately 1/3 the length of the wedge portion. Thus, for a wedge portion 24 having a length of approximately 5 inches (12.7 cm), the length of the anterior portion will be approximately 1.67 inches (4.2 cm) and the length of the posterior portion will be approximately 1.67 inches (4.2 cm). If the maximum thickness of that wedge portion 24 is approximately 0.25 inch (6.4 mm), the angle of taper of both the anterior and posterior portions will be approximately 8.51 degrees.

As discussed previously, the wedge portion 24 is designed to raise and support the medial and lateral longitudinal arches of the human foot, without actually contacting or pushing against these arches. To that end the wedge portion's construction automatically causes the locking of the midtarsal joint of the foot to increase stability of the entire foot. In so doing the support 20 of this invention can be beneficial for treating a plethora of foot pathologies that have been attributed to failure of the arch system of the foot and unlocking of the midtarsal joint. These pathologies include: plantar heel pain syndrome due to plantar fascia strain, tendon strain and rupture along the medial arch of the foot, hallux valgus and bunion deformity, metatarsalgia and neuroma in the forefoot, shin splint syndrome in running athletes and patellofemoral pain syndrome in running athletes.

Moreover, the support of subject invention provides stability to the arch without the risk of discomfort from ill-fitted arch supports. In fact, the support of this invention should work for all people, regardless of arch height or arch configuration and thus eliminate many problems of over-the-counter arch supports. In this regard, as will be appreciated by those skilled in the art, the problem with over-the-counter arch supports is the fit issue of a generic arch shape to a myriad of shapes of arches in the human population. The wedge of the subject invention, in contradistinction, does not require a fit to a specific arch shape.

Without further elaboration the foregoing will so fully illustrate our invention that others may, by applying current or future knowledge, adopt the same for use under various conditions of service.

I claim:

1. A support for a person's foot, the foot having an arch, a length and a width, said support being arranged for disposition within an article of footwear to effect raising of the arch of the person's foot by everting the forefoot of the person and inverting the rearfoot of the person to lock the person's midtarsal joint, said support comprising a base portion and a wedge portion, said base portion extending for substantially the length and width of the person's foot and having an upper surface and a lower surface, said wedge portion being disposed on said upper surface of said base portion and having a lateral side edge and a medial side edge, said entire wedge portion is designed to extend longitudinally from the base of all five metatarsals of the person's foot to the sulcus section of the person's foot, said wedge portion including a midline located centrally of said medial and lateral side edges, an anterior portion extending for approximately ⅓ the length of said wedge portion, an intermediate portion extending for approximately ⅓ the length of said wedge portion and a posterior portion extending for approximately ⅓ the length of said wedge portion, said anterior portion tapering downward in thickness anteriorly to the sulcus section of the person's foot, said posterior portion tapering downward in thickness posteriorly from said intermediate portion to the base of all five metatarsals, said wedge portion tapering in thickness along the entire length thereof from approximately said midline to said medial side edge, wherein said wedge portion is thickest at the midshaft of the fifth metatarsal at said lateral side edge of said intermediate portion and thinnest at the base of the second metatarsal and the lateral aspect of the first metatarsal.

2. The support of claim 1 wherein a portion of said wedge portion is of a constant thickness from said approximately said midline portion to said lateral side edge.

3. The support of claim 1 wherein said wedge portion tapers in thickness from said lateral side edge to said midline.

4. The support of claim 3 wherein said angle of taper from said lateral side edge to said medial side edge is constant.

5. The support of claim 1 wherein said wedge portion is of a length in the range of approximately 4 inches to approximately 5 inches (10.2 to 12.7 cm), a width in the range of approximately 2 inches to approximately 3 inches (5.1 to 7.6 cm) and a height in the range of approximately ⅛ inch to approximately ¼ inch (3.2 to 6.4 mm).

6. The support of claim 1 wherein said wedge portion comprises EVA foam.

7. A method for raising the arch of a person's foot by everting the forefoot of the person and inverting the rearfoot of the person to lock the person's midtarsal joint, said method comprising:
  (a) providing a support comprising a base portion and a wedge portion, said base portion having an upper surface, said wedge portion having a lateral side edge, a medial side edge, a midline located centrally of said medial and lateral side edges, an anterior portion extending for approximately ⅓ the length of said wedge portion, an intermediate portion extending for approximately ⅓ the length of said wedge portion and a posterior portion extending for approximately ⅓ the length of said wedge portion, said anterior portion tapering downward in thickness anteriorly to the sulcus section of the person's foot, said posterior portion tapering downward in thickness posteriorly from said intermediate portion to the base of all five metatarsals, said wedge portion tapering in thickness along the entire length thereof from approximately said midline to said medial side edge, said wedge portion being disposed on said upper surface of said base portion, and
  (b) disposing said support in an article of footwear, wherein said base portion extends for substantially the length and width of the person's foot, said entire wedge portion is designed to extend longitudinally from the base of all five metatarsals of the person's foot to the sulcus section of the person's foot, wherein the wedge portion is thickest at the midshaft of the fifth metatarsal at said lateral side edge and thinnest at the base of all the metatarsals and the lateral aspect of the first metatarsal.

8. The method of claim 7 wherein a portion of said wedge portion is of a constant thickness from said approximately said midline portion to said lateral side edge.

9. The method of claim 7 wherein said wedge portion tapers in thickness from said lateral side edge to said midline.

10. The method of claim 9 wherein said angle of taper from said lateral side edge to said medial side edge is constant.

11. The method of claim 7 wherein said wedge portion is of a length in the range of approximately 4 inches to approximately 5 inches (10.2 to 12.7 cm), a width in the range of approximately 2 inches to approximately 3 inches (5.1 to 7.6 cm) and a height in the range of approximately ⅛ inch to approximately ¼ inch (3.2 to 6.4 mm).

12. The method of claim 7 wherein said wedge portion comprises EVA foam.

13. The method of claim 11 wherein said wedge portion comprises EVA foam.

14. The method of claim 7 wherein said wedge portion comprises EVA foam.

* * * * *